United States Patent [19]
McCarthy et al.

[11] Patent Number: 6,153,721
[45] Date of Patent: Nov. 28, 2000

[54] PREPARATION OF POLYINDANEBISPHENOLS AND POLYMERS DERIVED THEREFROM

[75] Inventors: Thomas F. McCarthy, Lake Hiawatha; David B. Schwind, Blairstown; Gordon C. Smith, Arlington Heights, all of N.J.

[73] Assignee: Honeywell International Inc., Morris Township, N.J.

[21] Appl. No.: 09/031,286

[22] Filed: Feb. 26, 1998

[51] Int. Cl.$^7$ ............................. C07C 37/16; C08G 59/14
[52] U.S. Cl. ........................ 528/205; 568/719; 525/523; 478/413; 478/414
[58] Field of Search ............................ 528/205; 525/523; 568/719; 428/413, 414

[56] References Cited

U.S. PATENT DOCUMENTS

| | | | |
|---|---|---|---|
| 4,334,106 | 6/1982 | Dai ........................................ | 568/719 |
| 4,988,785 | 1/1991 | Paul et al. ............................... | 526/259 |
| 5,145,926 | 9/1992 | Patel et al. .............................. | 526/284 |

FOREIGN PATENT DOCUMENTS 864274   3/1961   United Kingdom .

OTHER PUBLICATIONS

Dittmer, Thomas, et al, "Cationic Polymerization of bis(1–alkylvinyl)benzenes and Related Monomers—Structure Elucidation of 1,1,3–trimetnyl substitued polyindane", Makromol. Chem, vol.190 , pp 1755–70; 1989.

Dittmer, Thomas, et al, "Cationic Polymerization of bis(1–alkylvinyl)benzenes and Related Monomers—Controlled syntheses of 1,1,3–trimetnyl substitued polyindanes", Makromol. Chem, vol. 190, pp 1771–1790, 1989.

Nuyken, Oskar, et al, "Cationic Polymerization of bis(1–alkylvinyl)benzenes and Related Monomers—Telechelics Containing Indane Units", Makromol. Chem, vol.192, pp 1969–79; 1991.

Nuyen, Oskar, et al, "Cationic Polymerization of bis(1–alkylvinyl)benzenes and Related Monomers—Synthesos of Monomers with Long alkyl side chains", Makromol. Chem, vol.192, pp 3071–78; 1991.

Nuyen, Oskar, et al, "Cationic Polymerization of bis(1–alkylvinyl)benzenes and Related Monomers—New Thermostable polyindanes", Makromol. Chem, vol.193, pp 487–500; 1992.

Wilson, John C., "Polyamides and Polyesters Derives from 1,1,3–trimethyl–3–(p–aminophenyl)–5–indaneamine and 1,1,3–trimethyl–3–(p–hydroxyphenyl)–5–indanol", Journal of Polymer Science, vol. 13, pp. 749–754, (1975), John Wiley & Sons, Inc.

Nuyken, Oskar, et al "Polymers With Indane Units by Cationic Polymerization", Makromol. Chem., Marcomol. Symp. vol. 60, pp. 57–63, (1992).

Brunner, H., et al "The Preparation and Structure of Linear Polymers from Di–isopropenylbenzenes"; Journal of Polymer Science, vol. XXVIII, Issue 118, pp. 629–631 (1958).

Imai, Yoshio, et al "Preparation and Properties of Aromatic Polyesters and Copolyesters Containing Phenylindane Unit" Journal of Polymer Science: vol. 22, pp. 1319–1325 (1984).

*Primary Examiner*—Terrel Morris
*Assistant Examiner*—John J. Guarriello
*Attorney, Agent, or Firm*—Curtis B. Brueska

[57] ABSTRACT

Novel polyindanebisphenols or PIBPs for the preparation of new and improved thermosetting polymers having the general formula of

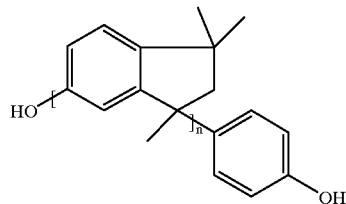

are provided. Also disclosed are thermoplastic or thermoset compositions prepared using the novel compounds of the invention, as well as methods of making and using the same. When copolymerized or reactive with other commercial resins such as, e.g., epoxy compounds, PIBP based polymers are characterized by high glass transition temperature ("Tg"), low dielectric constant, low moisture absorption, low coefficient of expansion, low cost, and can be processed on equipment typically used for the production of epoxy based laminates.

29 Claims, 3 Drawing Sheets

| N | 8 | 7 | 6 | 5 | 4 | 3 | 2 | 1 |
|---|---|---|---|---|---|---|---|---|
| MINUTES | 9.982 | 10.476 | 11.068 | 11.55 | 12.01 | 12.459 | 12.891 | 13.642 |
| EQUIVALENT WEIGHT | 1398 | 1240 | 1082 | 924 | 766 | 608 | 450 | 292 |

PREPARATION OF POLYINDANEBISPHENOLS AND POLYMERS DERIVED THEREFROM

BACKGROUND OF THE INVENTION

1. Field of the Invention

This invention relates to novel polyindanebisphenols which are useful in the preparation of thermosetting polymers and thermoplastics. The polyindanebisphenols ("PIBP") are prepared under acidic conditions from p-2-isopropenylphenol ("IPP") and 1,3-, 1,4-, or 1,2-diisopropenylbenzene ("DIPB") in quantitative yield. Molecular weight is controlled by the ratio of p-2-isopropenylphenol to diisopropenylbenzene. When copolymerized with other commercial resins such as cresol novolac epoxies, PIBP based polymers are characterized by high glass transition temperature ("Tg"), low dielectric constant, low moisture absorption, low coefficient of expansion, low cost, and can be processed on equipment typically used for the production of epoxy based laminates.

2. Description of the Prior Art

Phenolic-based polymer resins such as cresol-novolacs are commonly used in the production of thermosetting polymers for electronics (printed wiring boards, encapsulents, molding compounds, electrical insulation), reinforced plastics, including fiber reinforced plastics ("FRP"), aerospace, coatings (industrial, can), and adhesives. Previously available polymers based, e.g., on cresol novolac epoxies, suffer from a number of drawbacks. These include: (1) 1–2% moisture absorption; (2) low Tg; (3) undesirably high dielectric constant and (4) brittleness.

The importance of these properties can be appreciated by considering, for example, that for polymers, as the temperature of the polymer increases, one or more temperature points are passed at which there is a modulus loss due to a glass transition. Each such temperature point is thus described as a glass transition point or Tg. Therefore, a high Tg is a desirable feature permitting a printed wiring board or similar such construct to operate at higher temperatures, e.g., in an environment that includes active electrical and/or electronic components, while maintaining its structural integrity.

These problems can be overcome by using a phenolic based resin which has inherently low moisture absorption, high Tg, and low dielectric constant. Polyindanebisphenol ("PIBP") is particularly well suited to overcome these drawbacks because of the inherent stiffness of the indane polymer backbone and the hydrophobic nature of the polymer. However, due to the limitations of the previously available synthetic schemes, which resulted in prohibitive costs, PIBPs have not gained ready commercial acceptance for such purposes.

The synthetic chemistry of the polyindanes can be best appreciated by first considering the synthesis of a "polyindanebisphenol" having a single repeat unit. For example, 1,1,3-trimethyl-3-(p-hydroxyphenyl)-5-indanol ("TMHPI"), as shown below:

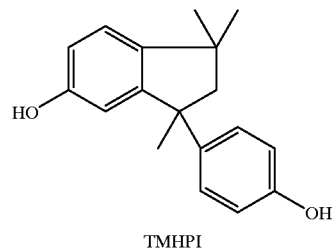

TMHPI is well known and has been utilized to prepare numerous thermosetting and thermoplastic polymers (U.S. Pat. Nos. 4,175,175, 5,145,926 and 4,988,785; Wilson, J. C., 1975 Journal of Polymer Science, Polymer Chemistry Edition, vol. 13, 749; Y. Imai and S. Tassavori, 1984, J. Polym. Sci., Polym. Chem. Ed., 22, 1319. However, none of these have attained a commercial status.

TMHPI is prepared from the precursor IPP, which is obtained first by cracking bisphenol A, having the following formula:

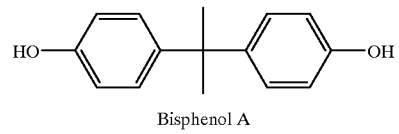

Bisphenol A

The cracking of bisphenol A is optionally conducted under acidic or basic conditions (e.g., in the presence of NaOH at 220° C.), yielding IPP, plus phenol; having the following formulas.

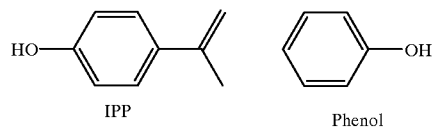

IPP          Phenol

The fact that the cracking process yields a mixture containing phenol, as a contaminant, has heretofore been considered a serious shortcoming of this process. IPP is not only heat sensitive, but it will readily polymerize under cationic, anionic, and free radical conditions. Consequently, while it has heretofore been taught that isolation of phenol from IPP is required to produce TMHPI, the isolation of IPP from phenol is in fact difficult to achieve in sufficient yield. After isolation of IPP, dimerization can then be conducted under acid conditions at mild temperatures to produce TMHPI. Thus, there is a longstanding need in the art for a method of avoiding the isolation of IPP from phenol in the preparation of indanes that are derived from IPP.

In addition, polymers based on TMHPI do not provide significant improvements to the parameters of moisture absorption, Tg, dielectric constant and brittleness. For example, when comparing similar polymers based on Bisphenol A or TMHPI, there is only a modest increase (10–30° C.) in glass transition temperature or Tg. For example, when TMHPI was polymerized with an equimolar amount of 4,4'-dichlorodiphenylsulfone to yield a polyethersulfone, a Tg of 215° C. was reported, which is only 30° C. higher than the commercial polyethersulfone-based on Bisphenol A (Tg=185° C.). In another example, of TMHPI shortcomings, when TMHPI is polymerized with the diglycidyl ether of tetrabromobisphenol A, a composition used for the preparation of flame retardant printed wiring board laminates, a glass transition of only 142° C. was obtained (U.S. Pat. No. 4,672,102). For this reason, polymers based on the TMHPI-type of indane structure have not achieved commercial success. Attempts to overcome these shortcomings have also led to investigation of polyindane compounds. The preparation of polyindane from the various DIPB compounds has been known since the late 1950's (Y. V. Mitin, N. A. Glukhov, Dokl., 1957, akad. Nauk, SSSR 115, 97; H. Brunner, A. L. Pallwel, D. J. Walbridge, 1958, J. Polym. Sci. 28, 629).

One class of polyindanes are the "unfunctionalized" polyindanes, i.e., polyindanes lacking additional functional moieties capable of crosslinking or curing in the presence of other potential copolymer/co-monomer resins, e.g., epoxies. Such unfunctionalized polyindanes can be prepared from a number of precursors, under cationic conditions, using either Lewis or Bronsted acids (O. Nuyken, G. Maier, D. Yang, M. Leitner, 1992, Makromol. Chem., Macromol. Symp. 60, 57–63; O. Nuyken, M. B. Leitner, and G. Maier, 1992, Makromol. Chem. 193,487–500; F. Gruber, O. Nuyken, 1989, Makromol. Chem. 190, 1771–1790; F. Griber, O. Nuyken, 1989, Makromol. Chem. 190, 1755–1770 and O. Nuyken, M. B. Leitner, G., Maier, 1991, Makromol. Chem. 192, 3071). Thus, any functionality which can be conveniently converted to the isopropenyl functionality is a suitable precursor to an unfunctionalized polyindane. For example, either of the following structures can be chemically converted into unfunctionalized polyindane:

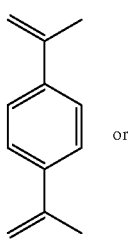

Formula A or

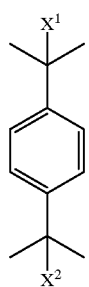

Formula B wherein $X_1$ and $X_2$ can be the same or different and can independently be any of Cl, OH, $OCH_3$ and/or $OCOCH_3$. Formula A is 1,4 diisopropenylbenzene and Formula B can be, e.g., ✗,✗ -dihydroxy-1,4, diisopropylbenzene, 1,4-bis (2-chloroisopropylbenzene), 1,4-bis(2-methoxy isopropylbenzene and 1,4-bis(2-acetoisopropyl benzene). The resulting polyindane has the formula:

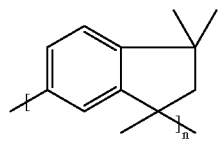

wherein "n" is an integer representing the number of repeats of the bracketed moiety or unit. However, this class of polyindane compounds has also, heretofore, failed to provide any practical and economical solutions for any of the above-mentioned problems in the art. Nevertheless, the compounds of Formulas A and B are readily employed as precursers to the compounds of the present invention, as described hereinbelow.

In particular, unfunctionalized polyindanes are claimed to have a Tg range from 220–320° C. and a decomposition temperature of 450° C. In fact, the art has described a broad range of molecular weights and glass transition temperatures, which attest to the difficulty in preparing pure polyindanes without some level of undesirable unsaturation. However, no commercial products have resulted from these efforts, due to the many shortcomings of this class of compounds. For example, the heretofor reported process is known to provide only low molecular weight polyindanes of this class, i.e., molecular weights of substantially less than 5,000 Dalton (see, e.g., O. Nuyken, et al., 1992, Makromol. Chem. 193, 487–500). Despite the suggestion that higher molecular weights might be obtained (e.g., Fritz et al., 1972, J. Polymer Science Part A-1, 10:2635–2378; D'Onofrio, 1964, J. of Applied Polymer Science 8:521–526; and Brunner et al., U.K. Patent No. 864,275, the previously provided polyindane polymers have been described as brittle, confirming undesirable mechanical properties.

In addition, these unfunctionalized polyindanes have other major drawbacks specifically related to printed wiring board applications. For instance, these compounds have no gel point, cannot be cured and do not crosslink. Thus, they exhibit unacceptably high coefficients of linear expansion and, without a curing step, cannot be used in traditional processes to produce laminate compositions. Further, polymers prepared from unfunctionalized polyindanes melt and flow at the temperatures used for soldering. In yet a further disadvantage, unfunctionalized polyindanes cannot be reacted chemically with other resins used to produce printed wiring boards.

"Functionalized" polyindanes were also tried in an attempt to produce less brittle polyindanes suited for the preparation of thermoplastics and thermosets. These were prepared by controlling the molecular weight and introducing functionality into the polymer, e.g., by introducing various substituent moieties to prepare polyindane derivatives. This strategy has been employed for the preparation of telechelics having terminal R groups, where R was $CH_3$, $NO_2$, $NH_2$, $CO_2H$, NCO, and COCl (O. Nuyken, D. Yang, F. Gruber, G. Maier, 1991, Makromol. Chem. 192:1969.

However, the available synthetic routes to obtain useful finctionalized polyindanes have remained too expensive for commercial purposes. Thus, only the methyl terminated polyindanes have been directly prepared using a cationic chain growth process involving diisopropenylbenzene and 1-isopropenyl-4-methylbenzene (Nuyken et al., 1992, Makromol. Chem., Macromol. Symp. 60, 57–63, Id.). Further chemical modification was necessary to obtain other functionalized polyindanes.

Thus, there remains a strong need in the art for polyindane compounds having all of the above-described desirable properties, e.g., reduced levels of moisture absorption; increased thermal stability; reduced dielectric constant and decreased brittleness, for this class of compounds, while being simple and economical to manufacture. In particular, there remains a need for functionalized polyindanes having all of the desirable properties of this class of compounds, and having a molecular weight of less than 2,000 which are not brittle and which can be reacted with other material, e.g., monomer compounds, for the preparation of thermosets and/or thermoplastics.

SUMMARY OF THE INVENTION

Accordingly, the present invention surprisingly provides compounds, including polymers, copolymers and polymer compositions, as well as processes for preparing the same, that solve these and other longstanding problems in the art. Thus, the invention provides for an unexpectedly improved type of polyindane, in the form of a polyindanebisphenol ("PIBP") compound of formula I:

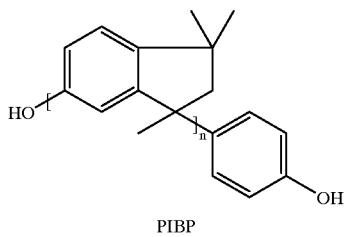

PIBP wherein "n" (also referred to herein as "(n)" for ease of identification) is an integer indicating the number of repeats for the bracketed moiety.

The invention also provides for polymers or copolymers prepared including the new polyindanebisphenols, as well as various types of compositions, e.g., laminates, prepared therefrom. Further, the invention provides for methods of preparing the inventive PIBP compound and polymer compositions including the same. PIBPs having an average number of repeating units of less than 2 will flow and process much like cresol novolacs but may not yield physical properties which are significantly better than polymers produced from Bisphenol A. For example, when PIBP is crosslinked with an epoxy resin to produce a laminate, the low molecular weight PIBP fails to provide significant improvement in moisture absorption and Tg properties over Bisphenol A based laminates. Thus, the invention provides for PIBPs having an average number of repeating units of two or more. As a consequence, the PIBPs of the invention readily provide the heretofore unobtainable linear hydroxy functionalized polyindanes, and provide simple and economical processes for preparing these desirable compounds, while avoiding the complexity of previously required substitutions on the indane structure. Therefore, the PIBP compounds according to the invention are readily prepared with molecular weights that will vary with the desired application and that will be primarily determined by the number of the repeat units.

As the number of repeating units (n) is increased to more than 10, on average, some of the resulting polymers will be brittle and, if processed from solution, will have high viscosities. Nevertheless, PIBPs having average repeating units (n), e.g., ranging from about 3 to about 1000, or greater, but preferably ranging from about 3 to about 25, and more preferably from about 3 to about 10, are readily prepared. Generally, as will be appreciated by the artisan, routine screening of a range of PIBP products, even those with (n) of greater than 10, will readily identify those polyindanes according to the invention with properties suitable for particular purposes.

Thus, the polyindanebisphenols of the invention will have (n) values consistent with molecular weights ranging from about 450 to about 200,000 Dalton, or greater. Preferably, the molecular weights of the polyindanebisphenols of the invention will range from about 450 to about 100,000 and more preferably from about 450 to about 2,000. In one preferred aspect, the molecular weight will range from about 600 to about 1700 Dalton.

Most preferably, the polyindanes of the invention have hydroxy equivalent weights that range from about 371 to about 924 grams. The hydroxy equivalent weight is the number of grams of polymer yielding 1 molar equivalent of hydroxy functionality, and is indicative of the hydroxyl concentration of the inventive polyindanebisphenols. In a most preferred aspect, the molecular weights of the polyindanebisphenols will range from about 370 to about 680 Dalton. In another aspect the invention also provides for novel polymer and/or thermosetting systems or compositions that are prepared by reacting one or more forms of the PIBP compounds of the invention and one or more additional suitable monomer compounds to form PIBP derivatives. The artisan will appreciate that, as described herein, and simply for ease of description, the term "polymer" or "copolymer" may also describe the comonomer compounds that are used to form the various polymers, copolymers and/or thermosetting systems or compositions according to the invention. Thus, additional polymer or copolymer compounds that are contemplated according to the invention include any materials suitable for the preparation of a useful derivative of the PIBP compounds of the invention and include, simply by way of example, art known polymer-forming monomers such as a polyetheretherketones, polyethersulfones, polycarbonates, polyesters, polyindanediallylethers, polyindanedicyanates, polyindanebisepoxies and/or any suitable variations, derivatives or combinations thereof.

In yet another aspect, the invention also provides for novel copolymers that include epoxy compounds such as, for example, cresol novolac epoxy resins, bisphenol F epoxy resins, brominated epoxy resins, polyglycidly amine epoxy resins, bisphenol A-based epoxy resins, fused ring aromatic epoxy resins, tetramethylbiphenyl-based epoxy resins, naphthalene or anthracene polynuclear epoxy resins, and mixtures thereof, as well as other types of epoxy resins, discussed in more detail hereinbelow.

Novel processes for preparing the PIBP compounds of the invention are also provided. Generally, the processes provide for the steps of (a) cracking bisphenol A to produce a mixture comprising p-2-isopropenylphenol and phenol, and (b) copolymerizing the mixture of step (a) with an isopropenylbenzene compound in suitable polymerization medium to yield PIBP.

For example, the above described copolymerization of step (b) is readily conducted under acidic conditions and in the presence of phenol. Further, in a preferred process, the copolymerization of step (b) can be conducted as a two-step process, so that the reaction is conducted in the presence of, e.g., an effective amount of trifluoroacetic acid followed by treatment with an effective amount of, e.g., sulfuric acid. Other options, in addition to acid treatment, include, simply by way of example, contacting the polymerization medium of step (b) with an effective amount of a strong acid cationic ion exchange resin, such as a sulfonic acid functionalized fluoropolymer, a sulfonic acid functionalized styrene-divinylbenzene (H) ion exchange resins, and/or mixtures thereof. In a further aspect of the invention, a heterogeneous acidic bentonite clay, a Ziegler type complex and/or mixtures thereof can also be employed in the copolymerization step. In a preferred aspect, the Ziegler type complex is LiBu-TiCl$_4$-HCl, Al(Et)$_3$Ti(OBu)$_4$-HCl and/or mixtures thereof are employed.

In another aspect, the p-2-isopropenylphenol is optionally separated from the phenol prior to step (b), by any suitable method or process. Generally, the polymerization medium includes any suitable solvent or solvents effective to solubilize the reactants and to support the polymerization reaction. Simply by way of example and without limitation, such a suitable solvent or solvent system includes nitrobenzene, benzene, toluene, hexane, 1,2-dichloroethane, tetrachloroethane, tetrachloromethane, and/or mixtures thereof. It will be appreciated that any art known polymerization accelerators, initiators and the like may be conveniently employed in conducting the polymerization process of the invention. Simply by way of example and without limitation, 2-ethyl-4-methyl imidazole and/or 2-ethyl imidazole may be readily employed for these purposes.

In yet another aspect, the invention also provides for improved laminates that employ and include the novel polyindanebisphenol compounds of the invention, as well as providing for methods of making such improved laminates. Given the novel polyindanebisphenols of the invention, the artisan will appreciate that any art-known methods may be employed to make any desired compositions benefitting from this improved material. Simply by way of example, one preferred method for preparing an improved laminate composition includes the steps of:

(a) mixing, in a suitable solvent, a polyindanebisphenol according to the invention with one or more other monomers that are suitable for forming a copolymer composition with the polyindanebisphenol;

(b) impregnating a suitable fibrous support material with the mixture of step (a)

(c) desolvating said impregnated support material under conditions effective to form a dry improved laminate composition.

BRIEF DESCRIPTION OF THE DRAWINGS

In order to better appreciate the nature of the invention, several figures are provided, which are as follows.

DETAILED DESCRIPTION OF THE PREFERRED EMBODIMENT

Accordingly, novel PIBP compounds having new and improved properties are provided, together with methods of making and using such PIBP polymers, as well as further polymer and/or copolymer products prepared from the novel PIBP compounds of the invention.

The PIBPs of the invention are generally prepared as follows. As described above, bisphenol A is first cracked into a mixture of phenol and IPP. In contrast to previous reports, the methods of the present invention do not require any separation of the IPP and phenol. Instead, the resulting mixture of phenol and IPP is directly copolymerized with DIPB in the presence of an organic solvent system (as discussed above) under acidic conditions, to yield a polyindane having a terminal phenol functionality, i.e., PIBP.

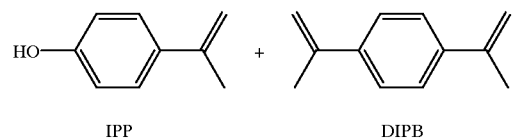

IPP                    DIPB

Surprisingly, the phenol resulting from the cracking of bisphenol A has been observed by gas chromatography not to participate in and/or interfere with the polymerization, and is conveniently removed from the polyindanebisphenol following polymerization. An optional feature of the invention provides for the addition of one or more aliphatic and/or aromatic substituent to the benzene ring of the diisopropenylbenzene, preferably before miking the diisopropenyl mixture. Reactions useful for making such an addition to the precursors of the polyindane or to the polymerization products are known to the art and include, e.g., electrophilic aromatic substitution reactions such as, halogenization, nitration, Friedel-Crafts acylation or alkylation, to name but a few. The polymer could also, simply by way of example, be crosslinked by Friedel-Crafts acylation and/or alkylation using ✕,✕ -dichloroxylene or diisoproenylbenzene.

Figure 1:
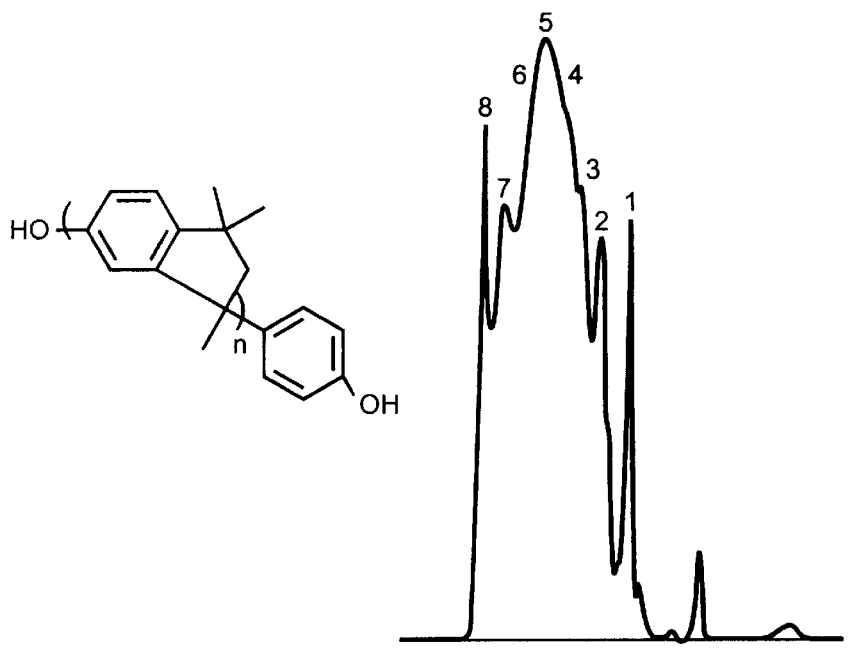
FIG. 1 illustrates size exclusion chromatography applied to the PIBP reaction product when the polymerization reaction was conducted with a 2.15:1 mole ratio of DIPB to IPP and indicates a nearly Gaussian molecular weight distribution of polyindanebisphenols, where the average molecular weight corresponds to an (n) ranging from about 4 to about 5.

Molecular Weight, Repeating Units (n) and Physical Properties of Resulting Polymers/ Copolymers It should be appreciated that the above-described polymerization reaction results in a nearly Guassian distribution of molecular weights, thus, in describing the reaction products, an average molecular weight and an average polyindane repeating unit is referred to. Further, the ratio of diisopropenylbenzene (DIPB) to p-2-isopropenylphenol (IPP) during the preparatory process defines the average molecular weight of the product PIBP compound. For example, when 2.15 moles of DIPB is polymerized with 1 mole of IPP, the product PIBP can be expected to have an average of approximately 4.3 indane repeating units. In this case (2.15:1 mole ratio), PIBP is obtained having a distribution of repeating units (n), from about 1 to about 8 repeating units and an average molecular weight of about 813. FIG. 1, illustrates size exclusion chromatography of the PIBP reaction product with a starting mix having a 2.15:1 mole ratio of DIPB to IPP. FIG. 1 shows a molecular weight distribution of polyindanebisphenols which is nearly Guassian, the average molecular weight of about 813 being equal, in this instance to an (n) ranging from 4–5. Thus, the desired molecular weight range of the PIBP may be varied to suit the application and the artisan will appreciate from this that the distribution of oligomers can be tailored according to the methods and proportions by which DIPB and IPP are combined.

Figure 2:
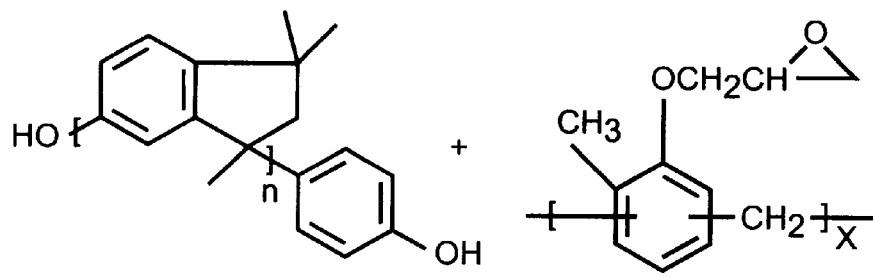
FIG. 2. illustrates the glass transition and onset of modulus loss for electrical laminates prepared as woven fiberglass impregnated with a copolymer of the invention.
Figure 2:
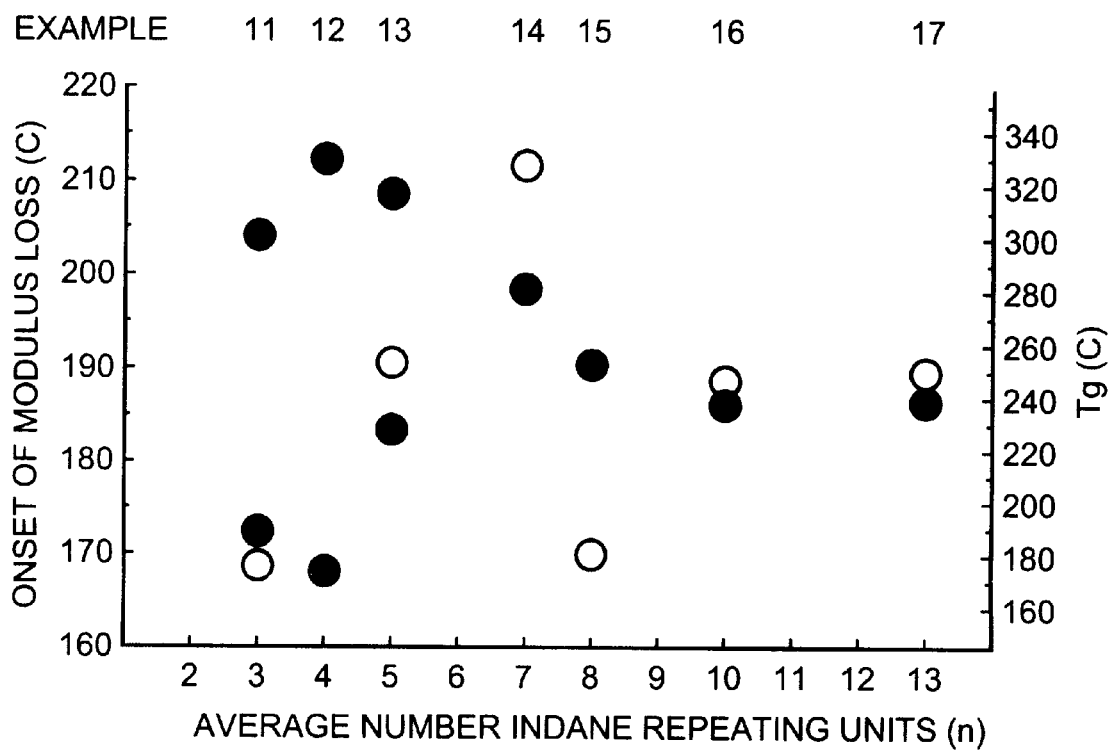

It has also been found that PIBPs having an average number of repeating units greater than 10 will, in some less desirable embodiments, yield brittle polymers, and if processed from solution will have high viscosities. At the other end of the distribution curve, PIBPs having an average repeating unit (n) of less than 2 will flow and process much like cresol novolacs but may not yield physical properties which are significantly better than polymers produced from Bisphenol A or TMHPI, as is the case when PIBP is crosslinked with an epoxy resin to produce a laminate, in which case the low molecular weight PIBP (n=1) does not show significant improvement over Bisphenol A based laminates with regard to moisture absorption and glass transition temperatures. This point is illustrated by Examples 11–17, hereinbelow, as represented in FIG. 2 and compiled in Table 2. FIG. 2 shows the glass transition temperatures and onset of modulus loss for electrical laminates based on a cresol novolac epoxy, woven fiberglass, and PIBPs of varying molecular weights, the exact compositions for which are summarized in Table 2. Low molecular weight PIBPs, when crosslinked with a cresol novolac epoxy, show two glass transitions corresponding to a polyindane phase and an epoxy phase. Higher molecular weight PIBPs, when crosslinked with an equivalent of a cresol novolac epoxy show only a single broad glass transition. The most desirable PIBP average molecular weight and (n) value will vary with the application.

Preparation of PIPB

The preparation of functionalized polyindane can be accomplished using a variety of Lewis or Bronsted acids. In preferred embodiments, these include trifluoroacetic acid (TFA), $SnCl_4$, $BF_3$, and $H_2SO_4$. Several alternatives to an acidic polymerization medium include, for example, art-known strong acid cationic ion exchange resins can be used, an example of which is Nafion® (Aldrich Chemical Company, Milwaukee, Wis.), a sulfonic acid functionalized fluoropolymer. Other alternatives to an acidic polymerization medium include standard sulfonic acid functionalized styrene-divinylbenzene (H) ion exchange resins. Heterogeneous acidic bentonite clays are also useful, for example, Super Filtrol F-I Ô (Engelhard Corporation, Jackson, Miss.). The heterogeneous catalysts have the advantage that they can be readily separated from the reaction mixture by filtration and can be reused repeatedly. In addition, Ziegler type complexes can be used to conduct the polymerization reaction. These include, for example, $LiBu-TiCl_4$-HCl or $Al(Et)_3Ti(OBu)4$-HCl. In another preferred embodiment, the polymerization reaction can be conducted with two acid steps. The first step is conducted in a polymerization medium that includes TFA. The TFA treatment is then followed by a post treatment with sulfuric acid. This two-step process has been found to be the most successful in avoiding products with incomplete indane ring closure and internal olefins along the polymer backbone, when the polymerization is conducted at room temperature, i.e., most successful in obtaining a polymer product that avoids unsaturation. Suitable polymerization solvents include any art known solvents that effectively dissolve the reactants and support the polymerization reaction. These include, simply by way of example, nitrobenzene, benzene, toluene, hexane, 1,2-dichloroethane, tetrachloroethane, and tetrachloromethane, to name but a few. Preferred polymerization solvents include nitrobenzene and 1,2-dichloroethane.

In a preferred embodiment, PIBP according to the invention is an ultrastable substrate for the manufacture of printed circuit boards. In particular, PIBP can be readily crosslinked with typical epoxy resins. These include, for example: cresol novolac epoxy resins, Bisphenol F epoxy resins, brominated resins such as brominated cresol novolacs, polyglycidly amine epoxy resins, Bisphenol A based resins, fused ring aromatic epoxy resins, tetramethylbiphenyl-based epoxy resins, naphthalene or anthracene polynuclear epoxy resins, resins having formulas according to one of the following general structures:

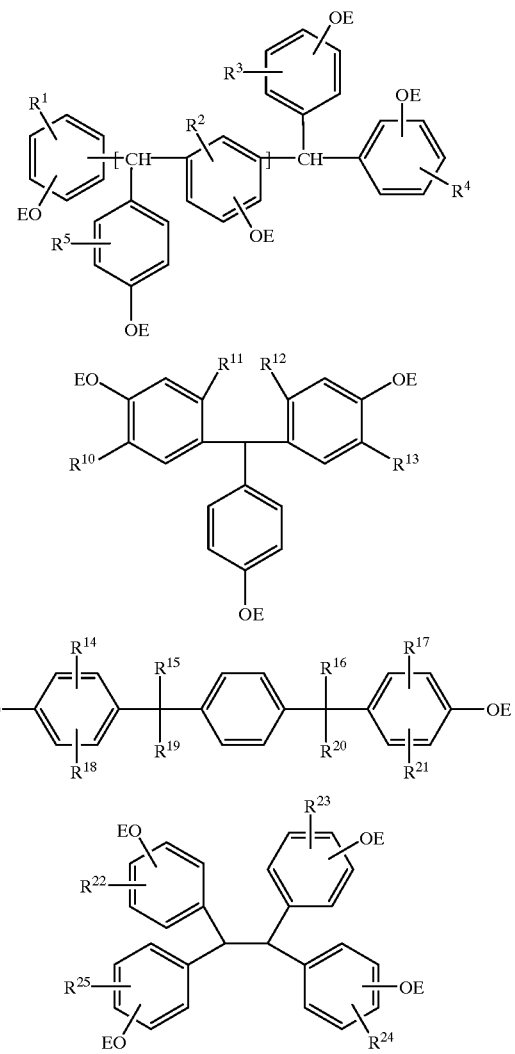

wherein each of $R_1$ through $R_{25}$ is the same or different and is independently one of: H, CH3, ethyl, propyl, isopropyl, isobutyl; and OE is

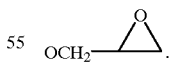

One advantage of using PIBP as a hardener in an epoxy resin system prepared according to the invention is that the resulting copolymer compositions exhibit desirably low moisture absorption values. Surprisingly, such a PIBP-based copolymer composition with a phenolic cured epoxy resin can have both a relatively high Tg value and a moisture absorption value of as low as 0.58% (preparation shown in Example 19, hereinbelow). This is a surprising result because the art had previously suggested that as the Tg value of a thermosetting resin is increased, the moisture absorption value is also increased. Based on the state of the art (M. Kaji, 1994, Polymeric Materials for Microelectronic Applications ACS Symposium Series 579 Hiroshi Ito, et al., Eds. Published by the American Chemical Society, Washington D.C.), a moisture absorption of 2–3 % would have been expected for a phenol/epoxy resin system have a Tg of 270° C. In a still further embodiment, epoxy copolymers that can be combined with a PIBP of the invention include, amine cured epoxy resins, polyamide cured epoxy resins, polyimide-epoxy blends, bismaleimide or phenyltriazine/epoxy blends, multifunctional or tetrafinctional epoxy resins, and styrene-maleic anhydride/epoxy resin blends, to name but a few additional art-known epoxy compositions.

The PIBPs according to the invention can also provide a number of additional useful embodiments. For instance, PIBPs of the invention can be converted into polyindanedicyanate and self-polymerized to form a triazine, or PIBP can be blended into a bismaleimide triazine resin system. Further still, a PIBP can act as a catalyst or, in larger quantities, can be crosslinked with bis(cyanate ester) derivatives of bisphenol A, novolac resins (Primaject-PT resin sold by Lonza, Fairlawn, N.J.), dicylcopentadienylbisphenol, and tetrabromobisphenol A. It is well known that phenolic resins accelerate the cyclotrimerization of cyanate esters. In addition to accelerating curing cycles, PIBPs according to the invention can, in a yet further embodiment, reduce the moisture absorption of the neat cyanate ester resins, by being incorporated into the cyclic trimer. Typical catalysts for these polymerizations are transition metal carboxylates or chelates such as zinc acetylacetonate, and ureas, to name but a few art known catalyst materials.

In other useful embodiments, PIBP can be converted to the following substances: A bis(cyanate ester) by reaction with cyanogen bromide or cyanogen chloride. An epoxy by reaction with epichlorohydrin and then reacted with an unmodified PIBP to yield a very moisture resistant high Tg epoxy resin. A bis (allylether) by reaction with allylchloride and then crosslinked using a free radical process or it could be cured by reaction with a bismaleimide such as methylenedianaline bismaleimide. A bis(allylether) derivative of PIBP can then be blended with a bis(maleimide)/diallylbisphenol A resin to yield a moisture resistant thermosetting resin for use in preparing printed wiring boards.

The compounds of the invention provide solutions to a number of problems long known to the art. For example, it is well known that epoxy containing materials are brittle and have poor resistance to crack propagation, the problem becoming increasingly worse with increasing glass transition. When rubber domains or thermoplastic domains are distributed within a highly crosslinked thermosetting matrix from the submicron to micron range, a rubber or thermoplastic may enable plastic flow, which serves to greatly increase the fracture energy. Thermosetting polymers based on PIBP having a minority component of an epoxy, for example, can be toughened in a number of ways. Typical strategies include the addition of reactive rubbers, modification with engineering plastics, and modification with non-reactive rubbers. Reactive rubbers include any rubbers which are carboxylic acid, hydroxyl, epoxy, amine, phenol, vinyl, or silane functionalized.

Segmented rubbers having a reactive functional group include, simply by way of example, dicarboxylic-acid-terminated oligo(butadiene-co-acrylonitrile), functionalized polybutadiene, dihydroxy terminated poly(propylene oxide)-block-poly(butadiene-co-acrylonitrile-block-poly (propylene oxide), dihydroxy-terminated pola ∈-caprolactone)block-poly(butadiene-co-acrylonitrile)- block-poly ∈-caprolactone), dihydroxy terminated oligo (alkylene oxide), phenol terminated poly(ether urethane), functionalized poly(dimethylsiloxane) and block coplymers contained compatibilizing carbon containing segments such as ∈-caprolactone.

An additional approach to the problem of toughening high Tg thermosets (thermosetting plastics) involves the addition of non-reactive rubbers. Preformed core shell latex rubber particles prepared from emulsion polymerization are typically used. The preformed core shell particles typically have a rubber core which might contain butylacrylate, butadiene, butadiene and styrene, while the shell might be a crosslinked or non-crosslinked thermoplastic such as PMMA, styrene, acrylonitrile, or glycidylmethacrylate. Polysiloxanes, fluooroelastomers, vegetable oils, and epichlorohydrin based rubbers have also been used.

Polyindane based thermosets can also be toughened by the addition of engineering thermoplastics. Typical thermoplastics include polyethersulfones, poly(etherimides), poly (aryl ether ketones), polyesters such as polybutylene terapthalate (PBT) or polyethylene naphthalate ("PEN"), poly (aryleneoxides) such as polyphenylene sulfide ("PPS"), polyphenylene oxide ("PPO"), polyhydantoin, and polycarbonates. Bisphenol A polycarbonates and amorphous polycarbonates including poly[bisphenol A carbonate]-co-4,4'-(3,3,5-trimethylcyclohexylidene)diphenol carbonate are especially preferred. Modified derivatives such as hydroxy, epoxy, amino, or carboxyl functionalized thermoplastics are also envisioned.

In further embodiments, the polyindanbisphenol compounds of the formula may optionally be prepared with substitution groups replacing one or both of the hydroxy moieties. Any art-known reaction may be employed to effect such a substitution, either for the polyindanbisphenol or precursors thereof. Simply by way of example, such substitutions will include isocyanate and any other art-known reactive moieties.

Composite Materials

Polymers based on PIBP can be used for the production of numerous composites. PIBP based polymers can be used to impregnate or coat any suitable substrates in need thereof, including, but not limited to, the following substrates: woven glass, non-woven glass, copper (a resin coated copper), quartz fabric reinforcement, cross plies of unidirectional tape, film, fiber, or paper (woven or non-woven) derived from polyester LCP such as Vectra® (Hoechst-Celanese, Bridgewater, N.J.) based on hydroxynapthoic acid and hydroxybenzoic acid; polyimide film including Kapton® (Dupont, Wilmington, Del), Upilex (UBE Industries, Tokyo Japan) based on biphenyltetracarboxylicdianhydride and either of p-phenylenediamine (PDA) or 4,4'-diaminodiphenylether, Thurmount® (Dupont, Id.); polyaramides such as Teijin's Technora® (Teijin America, Inc. New York, N.Y.) based on PDA and 3,4'-diaminodiphenylether, meta-aramids such as Nomex (Dupont, Id.) based on poly (m-phenyleneisophthalamide), and Teijinconex®, para-aramids including Kevlar® and Twaron® (Akzo, Dobbs Ferry, N.Y.) based on poly(p-phenyleneterephthalamide); and polybenzoxazole. These composites can optionally be filled with hollow glass spheres, quartz, fused spherical silica, mica, chopped fibers, clay, talc, and metal fillers to improve thermal conductivity.

Condensation Polymers

In a further set of useful embodiments, PIBPs according to the invention can be used for the production of condensation polymers having the following general structure:

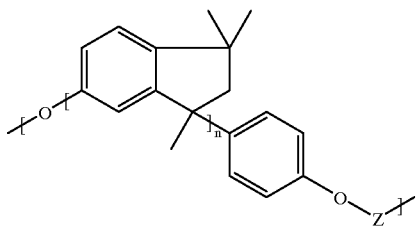

For example, in one particular embodiment PIBP can be copolymerized with difluorobenzoquinone or dichlorodiphenylsulfone to produce a polyetheretherketone or a polyethersulfone where z=

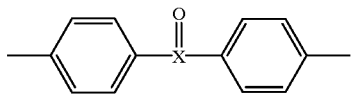

wherein X is S or C.

Alternatively, PIBPs according to the invention can be used to produce polycarbonates by reaction with phosgene gas or derivatives thereof, where x is a carbonyl group. In another alternative embodiment, PIBP can be copolymerized with Bisphenol A and phosgene.

BP can also be reacted with aromatic or aliphatic diacidchlorides, diacids, or the methylester derivatives thereof. Terephthaloyl chloride or isophthaloyl chloride are suitable aromatic diacidchlorides to produce a polyester having the structure described above where z=

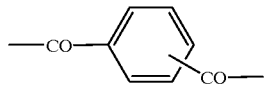

Thermoplastics or thermosetting resins based on polyindane can be processed from solution by coating or can be processed from the melt using the usual extrusion processes (injection molding, film extrusion, coextrusion, blow molding). When melt-processing thermosets, special care must be taken to control the advancement of the resin so that extrusion can be conducted at reasonable viscosities. Melt-processed thermosets can then be post-cured to obtain the final physical properties. PIBP based polymers can be coated using spray, dip, spin, powder, knife, pad, and the like. Films, coatings, or composites can then be laminated to other structures using standard lamination or roll lamination. The Following non-limiting examples serve to illustrate the invention.

EXAMPLES

Example 1

Cracking Bisphenol A

Bisphenol A can be cracked by any suitable art-known process. The following process is but one example of how this may be accomplished. 1 kg of Bisphenol A was placed in a 4 L flask with 3.5 g of dry NaOH. This flask was placed in a Kugelrohr distillation oven and connected to an 8" vigreux column which was connected to an external 4 L receiving flask. To the 4 L receiving flask was connected a 1 L flask which in turn was connected to an air driven motor via a glass shaft. The vigreux column was insulated and the 4 L receiving column was cooled with a dry ice/acetone mixture. To the 4 L receiving flask was added a gram of sodium bicarbonate and 0.2 g of t-butylcatechol. The system was evacuated to 200 mbar and the oven was heated to 225C. Upon melting of the bisphenol A the apparatus was rotated using the pneumatic motor. 850 gram of a mixture was collected in the receiving flask over a one hour time period. Analysis by gas chromatograph ("GC") showed a mixture containing 55.9% phenol, 41.2% IPP, the remainder being high boiling impurities. This mixture was then used directly without further purification. IPP is obtained fresh before each oligomerization and is typically present from 38–55% in the phenol/isopropenylphenol mixture.

Examples 2–8

Preparation of Polyindanebisphenols of Varying Molecular Weight

Figure 3:
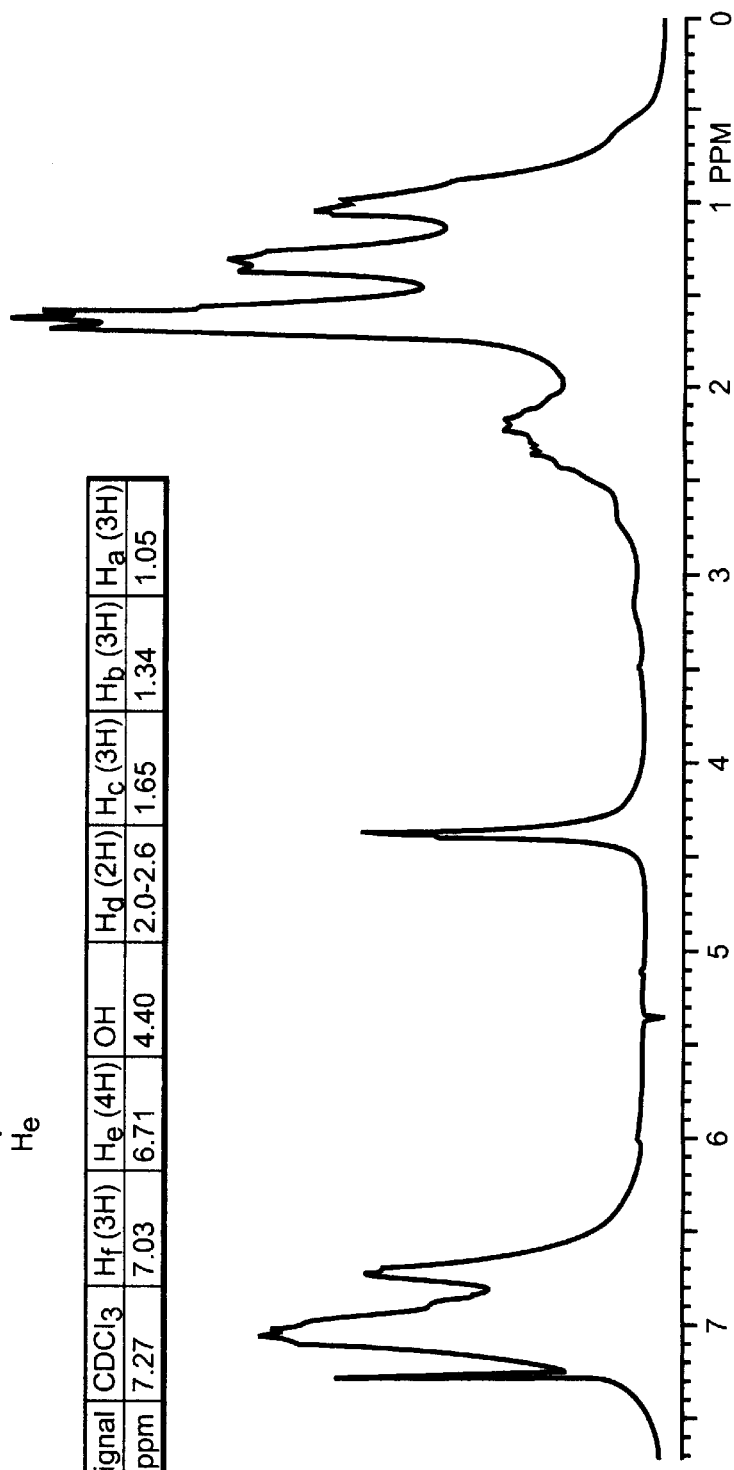
FIG. 3 is a proton NMR scan confirming the structure of the polymer prepared by the process of Examples 2–8.

The compounds designated as examples 2–8 were prepared by the following general procedure which specifically describes the preparation of the compound of Example 3. The compounds of Examples 2–8 are described in Table 1, below. 2 L of 1,2-dichloroethane and 40 g of trifluoroacetic acid were placed in a 5 L glass reaction kettle. The contents of two separate 1 L addition flasks, containing 819.9 g of 1,3-diisopropenylbenzene (DIPB) and 813 grams of product from the cracking of bisphenol A, respectively, were then added simultaneously to the stirred 5 L kettle, over a one hour time period, at room temperature. GC analysis indicated that the cracked bisphenol A product mixture contained 329.3 g IPP, the rest being >95% phenol. After complete addition, the kettle was stirred for one additional hour. The kettle was then cooled with ice, after which 46 g of concentrated sulfiuric acid was added. The kettle was then stirred overnight, after which a liter of water was added to the flask. The contents of the kettle were then transferred to a 13 L kettle equipped with an agitator and distillation head. 2 L of methanol was added to the flask. The organic solvents were then distilled from the kettle leaving a white polymer mass, and water. Phenol was azeotropically distilled from the flask by the continuous addition of water. Residual sulfuric acid was removed by washing the polymer with boiling water until a neutral pH was obtained. The polymer was dried under nitrogen at 80° C. The structure of the oligomer produced by the above process was confirmed by proton nuclear magnetic resonance spectroscopy (NMR) as shown in FIG. 3. Integration of the area under the peaks for the aliphatic and aromatic regions yielded a ratio of 2.21 (aliphatic:aromatic protons) Based on an average oligomer repeating unit number (n) of 4.2, this matches closely with the theoretical value of 2.21. The products are summarized below, in Table 1.

TABLE 1

| Example | DIBP (mol; isomer) | IPP (mol) | DIPB:IPP | Average MW | Average number of polyindane repeating units | yield (%) |
|---|---|---|---|---|---|---|
| 2 | 0.353 ; para | 0.249 | 1.4:1 | 576 | 2.8 | ND |
| 3 | 5.18 ; meta | 2.45 | 2.1:1 | 798 | 4.2 | 106 |
| 4 | 0.158 ; meta | 0.063 | 2.5:1 | 924 | 5.0 | ND |
| 5 | 5.68 ; meta | 1.63 | 3.5:1 | 1240 | 7.0 | 101 |
| 6 | 2.83 ; meta | 0.71 | 4.0:1 | 1398 | 8.0 | 97 |

TABLE 1-continued

| Example | DIBP (mol; isomer) | IPP (mol) | DIPB:IPP | Average MW | Average number of polyindane repeating units | yield (%) |
|---|---|---|---|---|---|---|
| 7 | 5.98 ; meta | 1.20 | 5.0:1 | 1714 | 10.0 | 102 |
| 8 | 5.37 ; meta | 0.83 | 6.5:1 | 2188 | 13.0 | 97 |

ND = not determined

Example 9

Preparation of PIBP Using 1,2-diisopropenylbenzene

Example 2 is repeated with the exception that 1,2-diisopropenylbenzene is used in the place of 1,3-diisopropenylbenzene.

Example 10

Preparation of PIBP Using Bentonite Clay 25 g TFA was diluted with 2.7 L 1,2-dichloroethane in a 5 L glass kettle. 840 g of 1,3-diisopropenylbenzene was combined with a 661 g mixture of phenol and p-2-isopropenylphenol (303.9 g, 2.26 mol) in an addition flask and added to the reaction kettle over a one hour time period. 250 g of SuperFiltrol F-Ô acid clay was added and the mixture was heated at reflux for 5 hours. The clay was then removed by filtration. Half of the 1,2-dichloroethane was removed by distillation. The remaining solution was then added to 16 L methanol, precipitating 589 g of product which was isolated by filtration (high molecular weight fraction, HMW1). The filtrate was distilled to dryness yielding another 530 g of product (low molecular weight fraction, LMW1). Total yield was 1,102 g or 96%. 4 g of LMW1 was further fractionated by heating in a water/methanol solution (20% water). The soluble fraction, LMW1A was separated from the insoluble filtered fraction, LMW1B. Methanol/water was distilled away from LMW1A. HMW1 was fractionated into a high (HMW1A) and low molecular weight fraction (HMW1B) using a similar procedure with the exception that a 20% acetone/methanol solution was used. All of the fractions were analyzed by size exclusion chromatography (SEC) to resolve the various polyindanebisphenol oligomers. SEC was conducted using a concentration of 5–6 mg of PIBP in tetrahydrofairan, a series of two polystyrene/divinylbenzene columns (5μ/100A PL-Gel and 5μ/50A PL-Gel) at a flow rate of 1 ml/min, with a Hewlett Packard HP1090 Liquid Chromatograph equipped with Chem Data Station. The separation method was adapted to APCI/SEC/Mass Spectroscopy (MS) using a Finnigan TSQ-7000 (triple stage quadrapole). APCI (atmospheric pressure chemical ionization)/infusion analysis in positive and negative ion mode was used on samples dissolved in THF using a concentration of 1 mg/ml. MS revealed a m/z 158 oligomer series. The highest molecular weight fraction (HMW1A) revealed an oligomer series having 3–8 repeating units. The lowest molecular weight fraction (LMW1A) revealed an oligomer series having repeating units from 1–4. The medium molecular weight fractions (HMW1B and LMW1B) revealed a distribution having an oligomer series from n=2–6. With the combination of SEC and MS, the oligomer series was resolved such that the individual polyindanebisphenol repeating units could be identified, as shown in FIG. 1.

Examples 11–17

Preparation of Printed Wiring Board ("PWB") Laminates Using PIBP and Cresol Novolac Epoxy The following is a general procedure for preparing the compositions of Examples 11–17, which specifically describes the preparation of PWB laminate prepared using the PIBP obtained in Example 3, shown above. 16.62 g of the product of Example 3 was added to 8.383 grams of a cresol novolac epoxy available from Ciba Geigy (ECN1299), 25 mg of 2-ethyl-4-methylimidazole (2,4-EMI), and 15 g of methylethyl ketone ("MEK"), yielding a clear solution upon mixing. The solution was coated onto 4 separate 6"×6" woven glass fabric using a Leneta wire wound rod. The resin impregnated glass fabric was allowed to dry, afterwhich the backside of the fabric was coated. The fabric was then heated in an oven at 190° C. to ensure the complete removal of solvent. The prepregs were then stacked one on top of the other, sandwiched between two pieces of PTFE release film and two polished chrome plates, and pressed at 220° C. for one hour. The laminates were then allowed to cool in the press, after which they were post cured in air at 270° C. for one hour. Moisture absorption was obtained by conditioning the samples in a oven at 85° C./85% humidity for 3 days, measuring % moisture uptake of the composite by Karl Fisher titration, and then ashing the composite to obtain the resin content. Glass transitions and the onset of modulus loss are shown schematically in FIG. 2. Dynamic mechanical analysis ("DMA") was conducted using a Rheometrics RDA-II in torsion rectangular mode at 1 hz. FIG. 2 shows a plot of the average number of indane repeating units or (n) verses the onset of modulus loss. The circles representing the properties of the products of Examples 11–17 are indicated on the Figure along the top "X" axis. As can be appreciated from FIG. 2, Tg values of between 200 and 300° C. can be readily obtained by using the compositions prepared above for Examples 11–17, as summarized in Table 2, as follows. For those compositions with more than one Tg value, e.g., the product of Example 12, the lower Tg is (generally) much weaker than the upper one, so that, for example, for the product of Example 12, the drop in modulus during the first Tg is generally much less pronounced than the modulus drop observed during the second glass transition at the higher temperature.

TABLE 2

| Example | PIDP | PIDP (%) | ECN1299 (%) | 2,4-EMI (%) | Resin Moisture Absorption (%) |
|---|---|---|---|---|---|
| 11 | 2 | 60.51 | 39.39 | 0.1 | ND |
| 12 | 3 | 65.47 | 33.50 | 0.1 | 0.99 |
| 13 | 4 | 69.16 | 30.74 | 0.1 | ND |
| 14 | 5 | 73.76 | 25.45 | 0.1 | 0.18 |
| 15 | 6 | 76.45 | 23.45 | 0.1 | ND |
| 16 | 7 | 79.58 | 20.33 | 0.1 | ND |
| 17 | 8 | 83.08 | 16.81 | 0.1 | ND |

ND = not determined

Example 18

PWB Laminate Based on PIBP and a High Purity Cresol Novolac Epoxy 17.56 g of the product of Example 3 was added to 7.43 g of a high purity grade cresol novolac epoxy available from Sumitomo Chemical as ESCN-195XHH, 0.1% 2,4-EMI. Laminates were obtained as above. Analysis by DMA yielded a very broad transition with two peaks, at 166° C. and 291° C. Thus, higher purity cresol novolac epoxies having a lower epoxy equivalent weight number (a higher concentration of epoxy) does not result in a substantial increase in glass transition temperature.

Example 19

PWB Laminate Based on PIBP and High Tg Epoxy 70.17 g of the product of Example 3 was added to 29.8 g of Sumitomo Chemical's TMH574 ( a phenol-based poly aromatic epoxy coupled with methylene bridges, having aliphatic substituents off the aromatic groups), 100 mg of 2,4-EMI, and 81.8 g of MEK. A laminate was produced as in Examples 11–17. Analysis by DMA showed a broad glass transition with two peaks, a minor shoulder at 187° C., the major peak occurring at 277° C. Samples of the 4 layer laminate were placed temperature and humidity controlled oven (85° C./85% humidity) for four days. Analysis by Karl Fisher titration yielded a moisture absorption of 0.10%. The samples were then ashed and found to contain 82.1% glass. The resin moisture absorption was then calculated to be 0.58% which is exceptionally low for a thermosetting resin having this high a glass transition temperature.

Example 20

Thin PWB Laminated Based on PIBP, High Tg Epoxy, and Polyaramide Non Woven Substrate Using a formulation consisting of 70.17 g of the product of example 3, 29.8 g of TMH574, 100 mg of 2,4-EMI, and 81.8 g of MEK, Thurmount®, available from Dupont, was coated in the following fashion: A six inch square piece of Thurmount was placed on the level glass surface of a Gardco acu-lab drawdown apparatus. To apply the formulation to the substrate, multiple passes with a meir rod were necessary to force all of the resin into the nonwoven. The substrate was then air dried until a non-tacky surface was obtained, after which the backside was coated. The sample was hung in air for 30 minutes to help drive off solvent. Next, the sample was hung in an oven at 200° C. for 4 minutes to drive off the remaining solvent and to thermally advance the resin. Finally the sample was placed between PTFE coated release film and polished chrome plates in a pre-heated 180° F. Carver press at 140 psi. The temperature was increased from 180° F. to 428° F. at a rate of 10+ F./min, and then increased to a dwell temperature of 518° F. for 4 hours.

Example 21

Preparation of PWB Laminate Containing a Rubber Impact Modifier

To 15.77 g of the product of Example 3 was added 4.72 g of Sumitomo Chemical's TMH574, 4.64 g of Shell Chemical's EPON Resin 58006, an epoxy finctionalized elastomer containing 40% by weight of a carboxy terminated butadiene-acrylonitrile elastomer, 25 mg of 2,4-EMI, and 20 g of MEK. A four layer laminate was prepared as in Examples 11–17. DMA analysis yielded a very broad transition with two discernable peak maxima at 143.2 and 313.2° C.

Example 22

Preparation of PWB Laminate Containing an Engineering Thermoplastic Polycarbonate Toughener To 15.79 g of the product of Example 3 was added 6.71 g of Sumitomo Chemical's TMH574, 2.5 g of an amorphous polycarbonate to toughen the laminate, poly[bisphenol A carbonate]-co-4,4'-(3,3,5-trimethylcyclohexylidene) diphenol carbonate pre-dissolved in 8.3 g of THF, 25 mg of 2,4-EMI, 1.9 g of additional tetrahydrofaran, and 10.23 g of MEK. A laminate was produced as in examples 11-17. 1 day moisture conditioning at 85° C./85% humidity yielded a moisture absorption of 790 ppm, which after ashing (25.3% resin), yielded a resin moisture absorption of 0.31%.

Example 23

Preparation of a Polyetheretherketone from PIBP 0.318 g (1.46 mmol) 4,4'-difluorobenzophenone, 2.0 g of a PIBP having a molecular weight of 1,374 (1.46 mmol), and 6 g diphenylsulfone are charged to a 3 neck flask equipped with a nitrogen purge, stirrer, and condenser. The reactants are heated to 180° C., after which 0.205 g of anhydrous potassium carbonate is added. The reactants are heated at 200° C. for one hour, 250° C. for one hour, and finally at 325° C. for one hour. The mixture is then cooled and precipitated into methanol to yield after filtration, the PIBP based polyetheretherketone.

Example 24

Preparation of a Polyethersulfone from PIBP

Into a 3 neck flask equipped with a mechanical stirrer, nitrogen purge, Dean-Stark moisture trap, is placed 3.0 g of a PIBP (2.2 mmol) having a molecular weight of 1374, 6 g dimethylsulfoxide, and 17 g of chlorobenzene. The mixture is heated to 80° C., after which 0.175 g of NaOH diluted with 0.175 g water is added over a ten minute time period. The system is refluxed as the water is removed as an azeotrope with the chlorobenzene. Refluxing from 120–140° C. is continued until all water is removed from the system. Residual chlorobenzene is removed from the system by heating at 160° C. A 50% solution of 0.623 g of dichlorodiphenylsulfone (2.2 mmol) in dry chlorobenzene is added over a ten minute period. The temperature is maintained at 160° C. for six hours, after which the product is cooled and precipitated into a water/methanol mixture yielding, after filtration, the PIBP based polyethersulfone.

Example 25

Preparation of a Polycarbonate from PIBP

A 250 ml 3 neck flask was charged with 10 g (13.4 mmol) of a polyindane, having a molecular weight of 742 g, dissolved in 110 ml of chlorobenzene. The flask was equipped with a stirrer, condenser, and heating bath oil. The flask was heated to 150° C., to which was slowly added, from an addition flask, 2.569 g triphosgene dissolved in 25 ml of chlorobenzene, over a 45 minute time period. The flask was refluxed for 1.5 hr, cooled, and the solution distilled to dryness for a yield of 8.745 g of polymer, after vacuum drying.

Example 26

Preparation of a Polyester based on PIBP

A 250 ml 3-neck flask was charged with 10 g (13.5 mmol) of PIBP (Mw=742), 100 ml chlorobenzene, mechanical stirrer, nitrogen inlet, and a reflux condenser. To the solution was added dropwise 2.736 g (0.135 mol) terephthaloyl chloride dissolved in 20 ml chlorobenzene over a 20 min time period. The vessel was refluxed overnight with noted viscosity increase. The vessel was cooled, and a distillation head was installed to drive off the chlorobenzene. When 80 ml of solvent had been removed, the reaction was allowed to cool and then was slowly poured into a vigorously stirred solution of 160 ml methanol and 40 ml water to yield a light brown precipitate. The precipitate was placed in a vacuum oven at 100° C. and dried overnight.

Example 27

Preparation of Polyindanediallylether 100 g of a PIBP having an average molecular weight of 932 is dissolved in 400 ml of n-propanol in a 3 neck round bottom flask equipped with nitrogen inlet, condenser, and stirrer. 8.77 g of NaOH pellets is added and the vessel contents are refluxed for one hour. After the solution cools to ambient temperatures, 20.38 g of allylchloride is added slowly over a 20 minute time period. The mixture is allowed to stir overnight and is later refluxed for three hours. The mixture is filtered to remove salt and the solvent removed by evaporation. The solid is extracted with water to remove residual salt. The polymer is then dissolved in acetone and precipitated into a water/methanol solution to yield the polyindanediallylether. A sample of the resin is added to an equimolar quantity of methylenedianiline bismaleimide and dissolved in MEK. The solution is coated onto woven glass fabric. The solvent is driven off at 175° C. The prepreg is placed between two PTFE release sheets sandwiched by two polished chrome plates, and pressed in a Carver press for 1 hr at 200° C. and 6 hr at 250° C. to yield a PWB laminate.

Example 28

Preparation of Polyindanedicyanate

A 250 ml 3-neck flask was charged with 10 g (13.5 mmol) of PIBP (Mw=742) in 40 cc. of acetone. To this was added 2.995 g (28.3 mmol) of BrCN. The flask was cooled –70 C. 2.72 g (26.9 mmol) of triethylamine was slowly added dropwise through an addition funnel over 20 minutes with a noticeable precipitate being formed. After addition, the reaction was allowed to stir for 20 minutes, the precipitate filtered and washed three times with 50 ml acetone. The filtrate was evaporated to dryness, yielding a light yellow solid, which was then dissolved in 150 ml diethyl ether, leaving behind undissolved triethylaminehydrobromide salt. The salt was filtered off, washed twice with ether and the filtrate evaporated and dried, yielding the purified polyindanedicyanate. Polyindanedicyanate is dissolved to 55% solids in MEK, to which is added 0.1% magnesium octoate as a catalyst and knife coated onto nonwoven fiberglass. The solvent is driven off at 80° C. in an oven and the resulting resin impregnated fiberglass if pressed between two polished chrome plates separated by PTFE release film at 250° C. for two hours. A bismaleimide cyanate ester blend is made by adding 1 part methylene dianaline bismaleimide to 9 parts of the polyindanedicyanate. A PIBP cyanate-epoxy blend is made by adding 25 parts of the diglycidylether of tetrabromobisphenol A to 75 parts of the polyindanedicyanate. The blends are processed into laminates under similar processing conditions as the neat polyindanedicyanate resin.

Example 29

Preparation of Polyindanebisepoxy ("PIBE")

A 250 ml 3-neck flask was charged with 50 ml of methylcellusolve, 65.15 g epichlorohydrin, and 100 g of PIBP, having a molecular weight of 742. The solution was heated to 60° C. and held for 3 hours. During the 3 hour period a total of 8.72 g of sodium hydroxide was added. The reaction was allowed to cool and became noticeably more viscous. The solvent was distilled off, after which excess epichlorohydrin was removed in a vacuum at 110° C., overnight. The product was extracted with water to remove trace quantities of salt.

Example 30

Preparation of a DWB Laminate Using PIBP and a Brominated Cresol Novolac Epoxy Resin 45 mg of 2,4-EMI, 9.02 g of 3 and 5.98 g of Bren 304, a brominated cresol novolac epoxy resin having a bromine content of 43.7% (Nippon Kayaku Co.) was dissolved in 10 g of MEK. The solution was coated onto woven fiberglass fabric using a wire wound rod, allowed to dry, and the backside coated in a similar fashion. The fiberglass samples were suspended in air and allowed to dry. The fiberglass sample was then placed in an oven at 200° C. for 17.5 minutes to advance the curing of the resin. The samples were then cut to a 6×6" size, stacked to form a two layer board, placed between two PTFE release sheets, which was further sandwiched between two polyimide sheets, and pressed at 5000 lbs for 1 hour. The samples were then cooled in the press.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. A polyindanebisphenol compound having the formula

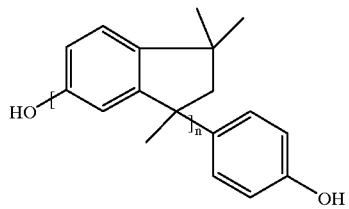

wherein n is an integer of at least two.

2. The polyindanebisphenol of claim 1 wherein n is an integer ranging from about 3 to about 1000.

3. The polyindanebisphenol of claim 2 wherein n is an integer ranging from about 3 to about 10.

4. The polyindanebisphenol of claim 1 having a molecular weight ranging from about 450 to about 200,000.

5. A thermosetting composition prepared by polymerizing the polyindanebisphenol compound of claim 1.

6. The thermosetting composition of claim 5 prepared by polymerizing the polyindanebisphenol with at least one polymer selected from the group consisting of a polyetheretherketone, a polyethersulfone, a polycarbonate, a polyester, a polyindaendiallylether, a polyindanedicyanate, and a polyindanebisepoxy.

7. The thermosetting composition of claim 5 prepared by polymerizing the polyindanebisphenol with at least one comonomer selected from the group consisting of a cresol novolac epoxy resin, a bisphenol F epoxy resin, a brominated epoxy resin, a polyglycidyl amine epoxy resin, a bisphenol A based epoxy resin, a fused ring aromatic epoxy resin, a tetramethylbiphenyl-based epoxy resin, a naphthalene or antliracene polynuclear epoxy resin.

8. The thermosetting composition of claim 5 prepared by polymerizing the polyindanebisphenol with a comonomer epoxy resin having a formula selected from the group consisting of

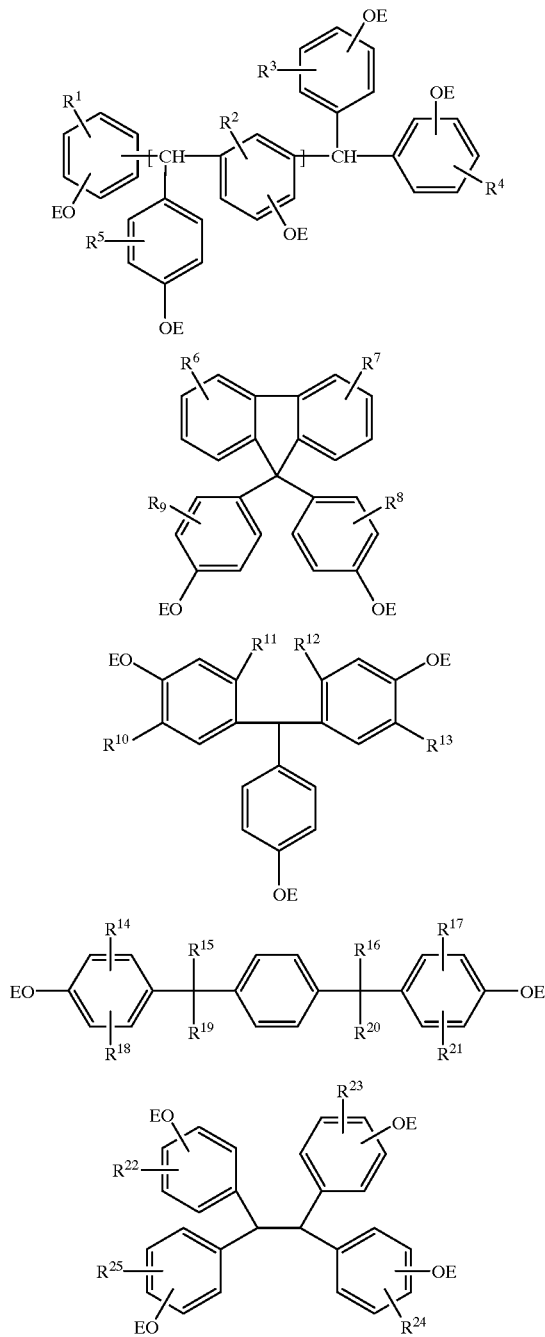

wherein $R_1$ through $R_{25}$ are independently the same or different and are selected from the group consisting of H, $CH_3$, ethyl, propyl, isopropyl, isobutyl, and wherein OE is

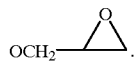

9. The thermosetting composition of claim 5 prepared by polymerizing the polyindanebisphenol with a brominated comonomer epoxy resin.

10. The thermosetting composition of claim 9 wherein said brominated epoxy resin is at least one compound selected from the group consisting of brominated cresol novolac epoxy resin, and tetrabromodiglycidylether bisphenol A.

11. A process for preparing a polyindanebisphenol compound by the steps of (a) cracking bisphenol A to produce a mixture comprising p-2-isopropenylphenol and phenol,(b) copolymerizing the mixture of step (a) with an isopropenylbenzene compound in a suitable polymerization medium to yield a polyindanebisphenol.

12. The process of claim 11 wherein said copolymerization of step (b) is conducted under acidic conditions and in the presence of phenol.

13. The process of claim 11 further comprising the step of separating the phenol from the mixture of step (a) prior to copolymerizing the mixture of step (a) with an isopropenylbenzene compound in a suitable polymerization medium to yield a polyindanebisphenol.

14. The process of claim 11 comprising the further step of recovering said polyindanebisphenol product.

15. The process of claim 11 wherein said diisopropenylbenzene is at least one compound selected from the group consisting of 1,2-diisopropenylbenzene, 1,3-diisopropenylbenzene, and 1,4diisopropenylbenzene.

16. The process of claim 11 wherein said copolymerization solvent of step (b) is acidified with an effective amount of an acid selected from the group consisting of a Lewis acid, a Bronsted acid.

17. The process of claim 11 wherein said acid is an effective amount of at least one acid selected from the group consisting of trifluoroacetic acid, $SnCl_4$, $BF_3$, and $H_2SO_4$.

18. The process of claim 11 wherein said copolymerization step (b) comprises treating the mixture of step (a) with a first acid comprising an effective amount of trifluoroacetic acid followed by treating the mixture of step (a) with a second acid comprising an effective amount of sulfuric acid.

19. The process of claim 11 wherein said copolymerization step (b) comprises contacting the polymerization medium of step (b) with an effective amount of a strong acid cationic ion exchange resin.

20. The process of claim 19 wherein said strong acid cationic ion exchange resin is at least one compound selected from the group consisting of a sulfonic acid functionalized fluoropolymer and sulfonic acid functionalized styrene-divinylbenzene (H) ion exchange resins.

21. The process of claim 11 wherein said copolymerization step (b) comprises contacting the polymerization medium of step (b) with an effective amount of at least one composition selected from the group consisting of a heterogeneous acidic bentonite clay and a Ziegler type complex.

22. The process of claim 21 wherein said Ziegler type complex is at least one compound selected from the group consisting of $LiBu-TiCl_4-HCl$, and $Al(Et)_3Ti(OBU)_4—HCl$.

23. The process of claim 11 wherein said polymerization medium comprises at least one solvent selected from the group consisting of nitrobenzene, benzene, toluene, hexane, 1,2-dichloroethane, tetrachloroethane and tetrachloromethane.

24. The process of claim 23 wherein said solvent is at least one compound selected from the group consisting of nitrobenzene, and 1,2-dichloroethane.

25. The process of claim 11 wherein said isopropenylbenzene compound is selected from the group consisting of

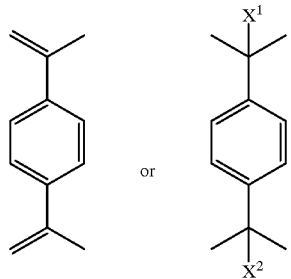

and mixtures thereof, and wherein $X_1$ and $X_2$ are independently the same or different are selected from the group consisting of Cl, OH, $OCH_3$, $OCOCH_3$.

26. The process of claim 11 wherein said isopropenylbenzene compound is 1,3-diisopropenylbenzene and the ratio of said 1,3-diisopropenylbenzene to said p-2-isopropenylphenol ranges from about 1.4 to 1 to about 6.5 to 1.

27. The process of claim 26 wherein the ratio of said 1,3-diisopropenylbenzene to said p-2-isopropenylphenol is about 1.2 to about 1.

28. A polyindanebisphenol compound prepared by the process of claim 11.

29. The method of claim 27 wherein said comonomer is at least one compound selected from the group consisting of an epoxy, and epoxy functionalized elastomer, and an amorphous polycarbonate.

* * * * *